(12) United States Patent
Bolla et al.

(10) Patent No.: US 6,737,262 B1
(45) Date of Patent: May 18, 2004

(54) ANIMAL FEED CONTAINING POLYPEPTIDES

(76) Inventors: Robert I. Bolla, 2220 S. 11th St., St. Louis, MO (US) 63104; Joseph E. Zahner, 3646 Dover Pl., St. Louis, MO (US) 63116; Monty S. Kerley, 2300 Rollins Rd., Columbia, MO (US) 65203

( * ) Notice: Subject to any disclaimer, the term of this patent is extended or adjusted under 35 U.S.C. 154(b) by 0 days.

(21) Appl. No.: 09/613,666

(22) Filed: Jul. 11, 2000

(51) Int. Cl.[7] .............................. C12N 1/00; C12N 1/20; C12N 1/14; A23K 1/60

(52) U.S. Cl. ...................... 435/254.2; 435/243; 426/53; 426/54

(58) Field of Search ...................... 426/53, 54; 435/243, 435/254.2

(56) References Cited

U.S. PATENT DOCUMENTS

| | | | | |
|---|---|---|---|---|
| 5,384,253 A | * | 1/1995 | Krzyzek et al. | |
| 5,559,223 A | * | 9/1996 | Falco et al. | |
| 5,985,605 A | * | 11/1999 | Cheng et al. | |
| 6,245,546 B1 | * | 6/2001 | Hansen et al. | |

* cited by examiner

*Primary Examiner*—David Guzo
*Assistant Examiner*—David A. Lambertson
(74) *Attorney, Agent, or Firm*—Dan Cleveland, Jr.; Lathrop & Gage L.C.

(57) ABSTRACT

The present invention relates to an animal feed made of an amount of cereal grain and a peptide or polypeptide expressed by a transformed organism, whereby the transformed organism can be included in the animal feed composition. The present invention also relates to a method for forming the animal feed wherein the method includes forming a transformed organism by transforming a yeast cell by inserting a nucleic acid molecule which will express a polypeptide desired for use in the animal feed.

20 Claims, 9 Drawing Sheets

HO gene Sequence (in yeast genome)

SEQUENCE LISTING

<160> NUMBER OF SEQ ID NOS: 13

<210> SEQ ID NO 1
<211> LENGTH: 6
<212> TYPE: DNA
<213> ORGANISM: synthetic construct -continued

```
<400> SEQUENCE: 1 ggtacc                                                                    6

<210> SEQ ID NO 2
<211> LENGTH: 6
<212> TYPE: DNA
<213> ORGANISM: synthetic construct

<400> SEQUENCE: 2 ggatcc                                                                    6

<210> SEQ ID NO 3
<211> LENGTH: 6
<212> TYPE: DNA
<213> ORGANISM: synthetic construct

<400> SEQUENCE: 3 gtcgac                                                                    6

<210> SEQ ID NO 4
<211> LENGTH: 6
<212> TYPE: DNA
<213> ORGANISM: synthetic construct

<400> SEQUENCE: 4 aagctt                                                                    6

<210> SEQ ID NO 5
<211> LENGTH: 8
<212> TYPE: DNA
<213> ORGANISM: synthetic construct

<400> SEQUENCE: 5 gcggccgc                                                                  8

<210> SEQ ID NO 6
<211> LENGTH: 37
<212> TYPE: DNA
<213> ORGANISM: synthetic construct

<400> SEQUENCE: 6
aaaagtcgac tcgagtttat cattatcaat actcgcc                                 37

<210> SEQ ID NO 7
<211> LENGTH: 39
<212> TYPE: DNA
<213> ORGANISM: synthetic construct

<400> SEQUENCE: 7
gatgatgcat cattttgttt atttatgtgt gtttattcg                               39

<210> SEQ ID NO 8
<211> LENGTH: 38
<212> TYPE: DNA
<213> ORGANISM: synthetic construct

<400> SEQUENCE: 8
aaaagcggcc gcctattaca ttttaatctt agttttcc                                38

<210> SEQ ID NO 9
<211> LENGTH: 37
<212> TYPE: DNA
<213> ORGANISM: synthetic construct
```

<400> SEQUENCE: 9
aatgatgcat catcatcatc atcacaagac aaagatc                37

<210> SEQ ID NO 10
<211> LENGTH: 50
<212> TYPE: DNA
<213> ORGANISM: synthetic construct

<400> SEQUENCE: 10
atcatcacaa gacaaagatc aaaatggttt ggaaaactaa gattaaaatg           50

<210> SEQ ID NO 11
<211> LENGTH: 43
<212> TYPE: DNA
<213> ORGANISM: synthetic construct

<400> SEQUENCE: 11
aatggaattc atgcatcatc atcatcatca caagacaaag atc             43

<210> SEQ ID NO 12
<211> LENGTH: 60
<212> TYPE: DNA
<213> ORGANISM: synthetic construct

<400> SEQUENCE: 12
tatcctcata agcagcaatc aattccatct atactttaaa agatcttttt tgtagaaatg      60

<210> SEQ ID NO 13
<211> LENGTH: 60
<212> TYPE: DNA
<213> ORGANISM: synthetic construct

<400> SEQUENCE: 13
acttttatta catacaactt tttaaactaa tatacacatt ccagcttgca aattaaagcc      60

ANIMAL FEED CONTAINING POLYPEPTIDES

SEQUENCE LISTING

This application is accompanied by a Sequence Listing for nucleotide sequences.

FIELD OF INVENTION

The present invention relates to an animal feed comprised of an amount of cereal grain and an amount of polypeptide, with such polypeptide expressed by a transformed organism. More particularly, the present invention relates to a genetically engineered yeast cell that expresses a polypeptide that is comprised of amino acids necessary to animal nutrition and growth, and methods related thereto.

BACKGROUND OF INVENTION

Cereal grains, such as corn, wheat, and rice, are fed to livestock and other animals, with consumption of these grains causing the animals to gain weight. Generally, consumption of such grains and/or grass results in sufficient weight gain, however, it is preferred to produce animals which have enhanced weight gain, as this increases the value of the animal. In other words, it is desired to produce animals of exceptional size and weight, which are comparatively larger than animals fed a normal diet. Increased weight gain can be promoted by ensuring that the animal receives necessary amino acids in desired amounts which help promote weight gain and are important nutritional constituents. It should also be noted that many amino acids which help enhance weight gain in various animals are not readily found in grass and cereal grains typically grains typically consumed by such animals. As such, farmers, ranchers, and feed lots supplement the animal's diet with various compositions which contain many of the desired amino acids.

One way to ensure that an animal's diet is supplemented with amino acids in amounts sufficient to result in weight gain, is to add amino acids derived from various natural sources to the animals' feed. Natural amino acid sources include offal from the slaughter of animals for human consumption, slaughter house sludge, poultry byproduct meal, or livestock or poultry litter. An example of how this material is used to promote growth can be illustrated by the use of the sludge. The sludge, which includes blood and feces from the floor of a slaughter house is gathered, treated, and mixed with animal feed to provide an animal with amino acids. Often, bacteria, such as E. coli, Salmonella, or other pathogens, are residents of such sludge and waste. If the sludge or waste is not thoroughly treated then infectious agents can be transmitted to animals that are fed the amino acid enhancements. The risk of transmitting infectious agents to animals is a growing concern as witnessed in Europe by the reaction to "mad cows' disease." Thus, it is greatly desired to have a method for supplying enhanced levels of amino acids to animals that does not require the use of amino acids derived from animal waste or sludge.

An alternative to using animal waste products is to produce the necessary and desired amino acids through genetic modification of various microorganisms. Currently, most amino acids used to supplement animal feed are synthesized by microbial fermentations. Such amino acids are then purified and can be added to animal feed as a supplement. Most of these amino acids form heterologous peptides. The use of these techniques has been undesired because the cost has made the addition of such amino acids prohibitive. Another problem is that the excreted amino acids must be purified. Most purification methods include stabilizing the amino acid using hydrochloride with lysine. This converts D isomers to L isomers. Consequently, it is further desired to have a method or composition for adding amino acids to animal feed that does not require a purification step and is economical and cost effective.

Purified amino acids produced by genetically modified organisms, typically bacteria, suffer from a number of other problems in addition to the cost. Often, purified amino acids are subject to degradative reactions during processing, such as maillard reactions. As such, it is hypothesized that providing the amino acids in a protein or polypeptide form would prevent or render such amino acids less susceptible to such degradative reactions. Often, pure amino acids are susceptible to incongruous absorption and catabolism by the intestinal or hepatic tissue of the animal consuming such products. For this reason, it is desired to have an amino acid or protein peptide that allows for easy digestion and absorption to be preferably accomplished congruently with other dietary proteins.

Finally, when using purified amino acids, only a limited number can be provided to the animal. As such, it is desired to have a method or composition that allows for a protein or polypeptide to provide second and third limiting amino acids.

The use of yeast and other microbes to express polypeptides is known. For example, U.S. Pat. No. 5,856,123 ('123) discloses a DNA expression vector for expressing a polypeptide. The vector includes bacterial and yeast origins of replication and genes for phenotypic selection of both bacterial and yeast moieties. The expression vector is designed for expressing A or B chains of human insulin. The patent does not disclose the use of a transformed yeast cell to produce the amino acids necessary to animal nutrition. Nowhere is an animal feed mentioned in the '123 Patent. While this particular patent is indicative of a variety of disclosed methods and compositions which discuss the use of transformed yeast cells for producing polypeptides or proteins, it is believed that the use of transformed yeast cells to produce animal feeds has not been disclosed. It is believed that the use of transformed organisms to produce polypeptides comprised of different amino acids desired in animal nutrition has not been practiced.

Yeast has also been known to be used to produce lactic acid. Metabolic engineering has focused on the production of heterologous proteins and peptides, including producing such proteins or peptides in transformed yeast. It is desired, however, to produce polypeptides comprised of more than one amino acid residue.

For these reasons, it is desired to have a method for producing an animal feed that is economical and does not run the risk of microbial contamination. Additionally, it is desired to have an easily activated vehicle that readily delivers amino acids for animal consumption. Most importantly, it is desired to have an animal feed having desired types and concentrations of amino acids.

SUMMARY OF INVENTION

The present invention relates to an animal feed that includes an amount of cereal grain and a peptide or a polypeptide expressed by a transformed organism. The polypeptides can be separated from the transformed organism, or the transformed organism and polypeptide, together, can be added to the cereal grain. The present invention further relates to the transformed organism which is preferably a yeast cell having a nucleic acid polymer inserted into the yeast cell chromosome, whereby the nucleic acid molecule can be expressed to form a peptide or polypeptide useful in the nutrition of an animal. The nucleic acid polymer will preferably be comprised of a fragment for expressing the polypeptide, a promoter that can be induced, and an identifier which is preferably either histidine or uracil related. The promoter is preferably a GAP promoter. While yeast is the preferred organism to be transformed, any of a variety of other microorganisms that can be consumed by animals and which can be transformed may also be used.

The present invention also relates to a method for forming the transformed organism and a method for forming the animal feed comprised of the cereal grain and either the transformed organism or the expression product of the transformed organism. The method includes preferably forming a synthetic nucleic acid polymer and attaching a promoter and stop sequence thereto. After formation of the nucleic acid polymer, the method will further include inserting the polymer into a vector and transforming a host organism. Alternatively, the integration construct can be placed in the host organism by using electro-poration. It is preferred if prior to transformation, the nucleic acid polymer is annealed or attached to primers which will allow for the formation of an integration construct. The resultant integration construct is then placed in a transfer vector and used to transform the host cell organism. It should also be noted that it is preferred if the transformed yeast cell is haploid, because it is preferred to insert the nucleic acid polymer into the chromosome of the host. Diploid hosts can be used if the nucleic acid polymer is inserted outside the chromosome.

The polypeptide or peptide expressed by the transformed organism will be at least two amino acids long, and will be comprised of at least two different amino acid residues. More preferably, the polypeptide will be between 20 and 30 amino acids long and will be comprised of at least five different residues. The amino acids to be expressed by the transformed organism will be selected in advance to ensure that, when consumed, the animal will receive maximum nutritional benefits so as to enhance growth and weight gain. Such amino acids can be selected according to the animal's age and particular nutritional needs.

The present invention is advantageous because it allows for an economical way to produce amino acids, specifically polypeptides, that can then be used to supplement an animal's diet. The present invention is especially advantageous because the transformed host organism can also be fed to the animal. This means purification steps can be eliminated so that costs are minimized. The invention is further advantageous because the amino acids are readily absorbed and do not readily degrade. Also, the polypeptide will include amino acid residues not typically found in other animal feeds or supplements. Thus, an animal feed is produced that is more nutritionally complete because it contains desired amino acids believed not to be found in other animal feeds.

DETAILED DESCRIPTION OF INVENTION

Figure 1:
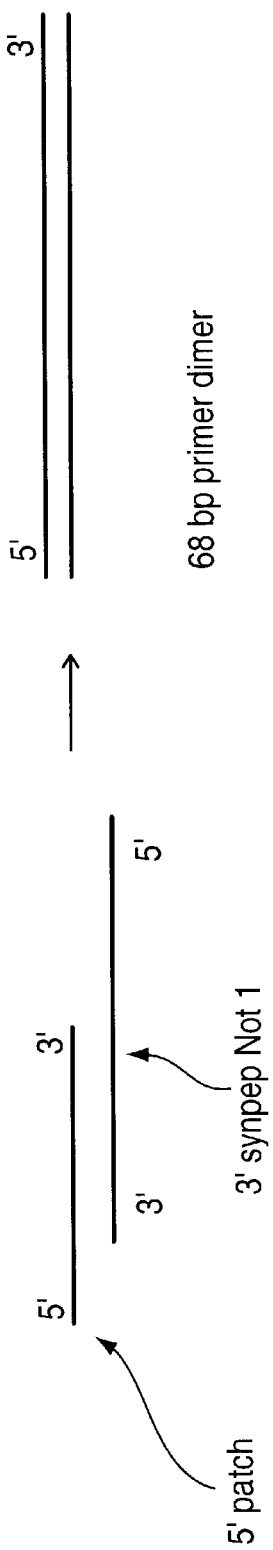
FIG. 1 illustrates PCR construction of a synthetic gene for encoding a synthetic peptide, whereby a 68 bp primer dimer is formed.

The present invention relates to an animal feed comprised of an amount of cereal grain and an amino acid polymer, with it more preferred for the animal feed to be comprised of a host for expressing the polymer. More preferred is for the animal feed to be comprised of cereal grain and at least one additive peptide, polypeptide, or protein. The present invention also relates to a method for forming the animal feed. Included in the method for forming the animal feed is a method for introducing a nucleic acid molecule or polymer into a host organism, with expression then occurring in the host organism to form the peptide or peptides. It is preferred if a transformed yeast cell is formed for expressing the peptide. Another aspect of the invention relates to a vector for introducing the nucleic acid molecule into the host organism, with the vector having a synthetic gene for expressing a peptide or, at the very least, containing a nucleic acid molecule that can be expressed to form a desired peptide. Preferably, a synthetic gene or genetic construct comprised of the nucleic acid molecule and a promoter can be inserted into the vector, with the gene designed to express a specific group of amino acids. Further, the present invention relates to a gene, and more particularly a nucleic acid polymer, that when expressed will produce a desired peptide designed to maximize weight gain and growth in an animal. It is preferred if the animal feed is comprised of an amount of the grain and an amount of the peptide, whereby the peptide is produced by a transformed yeast cell, with a vector or near DNA fragment containing a synthetic nucleic acid polymer used to transform the yeast cell that can then be expressed to form the peptide.

The animal feed, as mentioned, is comprised of an amount of grain and an amount of a product expressed by a microorganism, preferably an amino acid polymer. Preferably, the amino acid polymer is a peptide or polypeptide, although proteins may also be useful in the present animal feed. The feed will contain at least one peptide, but may contain multiple separate peptides, with each separate peptide comprised of different amino acids. The animal feed is designed to provide animals with necessary amino acids so that growth and health can be enhanced when the animal consumes the present feed on a regular basis.

The feed is intended for consumption by livestock, companion pets, aquacultures, and captive animals, with livestock including poultry, bovine, ovine, porcine, and equine members. Captive animals will include those that are maintained in zoological parks or hunting or conservation reserves. Companion pets include felines and canines, and aquaculture is defined to include all species of fish or invertebrates used in food production for which a soy-based diet is being used or may be used with nutritional adjustment. Essentially, any animal that can be fed on a consistent basis grain based animal feed having an amount and desired concentration ratio of amino acids, preferably peptides, can be fed the present inventive feed. All of these different types of animals will consume different types of cereal grains and have different amino acid requirements. Thus, according to the present method, animal feeds designed to meet the nutritional requirements of individual species can be manufactured by expressing nucleic acid polymers to produce desired polypeptides, with the nucleic acid polymers being either synthetic, isolated and naturally occurring, or combinations thereof.

The cereal grains which can be used to form the feed of the present invention include, but are not limited to, soybean, corn, barley, rice, wheat, oats, millet, maize, sunflower, canola, grass, and combinations thereof. The expression products, preferably a peptide or peptides, that are mixed with the cereal grains to form the present feed can be specified so that dependent upon the particular animal to which the animal feed is fed, necessary amino acid constituents can be specified. More particularly, amino acids necessary for weight gain and general health can be specified, so that the feed is animal specific. Further, the feed, in particular the peptides, can be adjusted so that dependent upon the age or development of the animal, particular types and concentrations of amino acids can be included in the animal's diet.

Any expression product that promotes increased weight gain and better health in the animal being fed can be mixed with the grain. The preferred expression product is a peptide or polypeptide, with the peptide preferably exogenous to the host organism. A peptide is defined herein to be comprised of at least two amino acids attached to one another via a peptide bond or other covalent bond, with the polypeptides typically comprised of between about 10 and about 30 amino acids. The amino acids are defined as containing an α-amino group ($NH_2$) and an acidic a-carboxyl group (COOH), with it known that there are 20 identified naturally occurring amino acids in eukaryotic proteins, along with L and D isomers. The available amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. As such, the peptides are strings of connected amino acids. The amino acids which form the peptide can be all the same or combinations of different L or D amino acids.

The first step necessary to forming the animal feed and providing a particular animal with desired expression products involves selecting a desired cereal grain. The cereal grain selected is dependent upon the particular dietary requirements of the animal to be fed. After the cereal grain is selected, the particular expression product, typically a polypeptide, necessary to promote increased weight gain must be determined. This generally requires identifying desired and particular amino acids and the concentration and ratio of such amino acids. Once determined, a peptide or polypeptide comprised of these amino acids must be formed. Such amino acid information is available in standard veterinary and animal science protocols, and can be used to either select a naturally occurring nucleic acid polymer, or to form a synthetic nucleic acid polymer. For example, the following table shows the ideal amino acid requirements for three different species of adult animals.

|  | Poultry | Swine | Dairy Beef |
| --- | --- | --- | --- |
| Lysine | 100 | 100 | 100 |
| Methionine/Cysteine | 60 | 33 | 20 |
| Threonine | 60 | 0 | 0 |
| Valine | 75 | 0 | 0 |
| Isoleucine | 60 | 0 | 0 |
| Arginine | 80 | 0 | 100 |
| Tryptophan | 20 | 0 | 0 |
| Histidine | 0 | 0 | 35 |

Note that amino acid requirements for all animals are determined in view of providing the animal with 100% of the recommended amount of lysine. Thus, the listed amino acids are the desired weight percent added as compared to lysine.

As can be seen, an adult chicken requires lysine, threonine, methionine, etc. A poultry feed preferably contains these percentages of amino acids in amounts sufficient to ensure all consuming subjects will receive the desired amount of specified amino acids. The amino acids are delivered as peptides, polypeptides, or proteins. A preferred poultry feed will be comprised of ground corn or soybean meal and a polypeptide, with the polypeptide preferably comprised of the following amino acid units: 3 methionine, 6 histidine, 6 lysine, 2 threonine, 2 isoleucine, 1 valine, and 1 tryptophan residue. Other acceptable polypeptides for use with the animal feed are listed in Example 9.

To have a desired peptide expressed, it is necessary to have a nucleic acid polymer, also known herein as a gene, for expressing such peptide. Acquisition of such gene is accomplished, for example, by isolating a gene or a host organism that expresses the gene, isolating a nucleic acid molecule or polymer which encodes for a desired peptide and forming a synthetic gene based on this molecule or polymer, forming a synthetic nucleic acid molecule or polymer which encodes for a desired peptide and forming a synthetic gene, or isolating a nucleic acid molecule or polymer ligating a synthetic nucleic acid molecule or polymer thereto and forming a synthetic gene. Dependent upon the peptide, which will contain the desired amino acids, concentrations, and ratios thereof, either a nucleic acid molecule or polymer that encodes the peptide is isolated, a nucleic acid molecule or polymer is formed, or a synthetic nucleic acid molecule or polymer is attached to an isolated nucleic acid molecule. Because the specific concentration and combination of amino acids often is not expressed by a naturally occurring nucleic acid molecule, it is generally necessary to form a synthetic nucleic acid molecule or polymer. Keep in mind, any of a variety of nucleic acid molecules may express the same desired peptide. The amino acids which comprise the peptide can be arranged in any order, meaning the codons for the amino acid can be arranged in a variety of orders in the nucleic acid molecule or polymer. Note that a codon of 3 nucleic acid bases might be considered a molecule of a nucleic acid, but several codons is generally considered a nucleic acid polymer.

If a nucleic acid polymer that expresses the desired peptide is available, standard protocols for isolating such molecule are followed, including removing the polymer from the host genome. This method will include using an enzyme (restriction endonuclease) to cut the nucleic acid fragment out of the host genome or episomal DNA molecule. More particularly, the fragment is identified and a restriction digestion is conducted to isolate the fragment.

Any of a variety of restriction enzymes can be used as long as the fragment is cut and isolated from the host. An example of a suitable protocol was published in Birren et al. (1997).[1,2,3]

Note that if a host organism exists that is non-toxic, easily grown, can be fed to animals, and contains an easily expressed nucleic acid polymer that expresses a desired peptide, then transformation is not necessary. In this case, the polymer merely needs to be expressed and the product mixed with the feed. Further, the transformed organism can be inducible or constitutive dependent upon what is desired. Typically, the isolation of such organism is unlikely because of the necessity of expressing a wide range of peptides and polypeptides; however, if such an organism exists, it can be used in the present invention.

Conversely, if the nucleic acid molecule or fragment is not naturally occurring, it is necessary to make a synthetic fragment. Typically, it is necessary to form the synthetic fragment, as the preferred type and concentration of amino acids are not available as a result of expression of the nucleic acid molecule or polymer. It is generally necessary and preferred to make a fragment that, when expressed, results in a desired peptide or polypeptide. A standard protocol for forming such fragment is found in Birren et al. (1997).[1,2,3] Once the fragment is formed or isolated, it is necessary to transfer the fragment to a host organism. This may require a number of steps. It is most preferred to form a synthetic fragment, but isolated nucleic acid molecules or polymers and host organisms can be used.

The synthetic fragment for expressing the peptide preferably is comprised of two single stranded fragments annealed to one another, but fragments that are initially double stranded may also be used. The most preferred method for forming the fragment is initiated by acquiring single stranded primers which will anneal to one another to form a double stranded fragment. The primers are comprised of nucleic acids, more specifically codons, which express the desired peptide. The primers are formed according to the desired specification related to the expressed peptide. The protocol for forming a primer comprised of the desired nucleic acids is detailed in Gait 31. Additionally, the primers have recognition sites whereby an endonuclease recognizes and cuts the molecule at the specific site. One primer should be a 3' to 5' strand having a known nuclease site; for example, a 3' fragment having an Not I cut site. The other primer should be a 5' to 3' fragment having a known nuclease site. The primers are combined and then passed through a PCR process to form a primer dimer. Increased amounts of product will be formed as a result of the primers being subjected to the PCR process. The primers will anneal to one another to form the primer dimer. The primer dimer will contain nuclease recognition sites on each end and codons for expressing the desired peptide. Also, the primer dimer will preferably have blunt ends.

If the primers do not anneal, it may be necessary to use a patch to promote attachment of the primers. The patch, like the primers, will be comprised of nucleic acids designed to express a desired peptide. Attachment results from first annealing the patch to a primer and passing the product through a PCR step. The patch primer product is then annealed to another primer and again passed through the PCR. An illustration of this involves a primer patch and a primer coding for part of the peptide annealing the two and amplifying to form a 68 base pair (bp) primer dimer. The 68 bp primer dimer is then combined with a 5' Synpep Eco R1 primer and passed through the PCR process to form a 91 bp synthetic peptide fragment having an Eco R1 site and a Not I site. Additionally, contained in the fragment is a Kozack consensus for translation start.

While the preferred method for forming a synthetic nucleic acid molecule involves annealing two primers containing the desired codons, other methods may be used. In fact, any method can be used that will result in a nucleic acid molecule or fragment that expresses the desired peptide.

PCR (Polymerase Chain Reaction) is a system used for DNA replication that employs the essential enzyme of cellular DNA replication, DNA polymerase. The primers used to form the primer dimer bracket the nucleic acid molecule that expresses the peptide and serve as points of attachment for the polymerase. Amplification occurs so that a sufficient amount of material is available to continue the transformation procedure. The procedure for a typical PCR reaction can be found in Innis et al. (1990)[11].

Once the fragment is formed or isolated, it is necessary to attach a promoter to the fragment, if one is not present, so that the nucleic acid polymer can be turned on or transcribed and expression of the polypeptides will occur. A different, yet equally acceptable approach involves inserting the synthesized fragment into a naturally occurring nucleic acid polymer in such a way that the fragment is controlled by the polymer's promoter sequence. The promoter is the region of a nucleic acid polymer required for maximum expression of the gene. The promoter can be isolated or can be synthesized, based on the known sequence of an expressed gene of prokaryotic or eukaryotic origin.

Promoters can be induced or constitutive. An induced promoter means it can be turned on in response to a constituent that induces activation. Conversely, a constitutive promoter is not turned on or off, but continues to cause expression of the fragment. An example of a constitutive promoter is where the gene construct contains a transcription elongation promoter (TEF). Either type of promoter is acceptable as long as suitable expression of the polypeptide occurs. In the present invention, a GAPDH (glyceraldehyde-3-phosphate dehydrogenase promoter) promoter of 679 nucleic acid base pairs is most preferred. This is a constitutive promoter.

Another preferred method for expressing the peptide or polypeptide relates to adding $Cu^+$ to the medium in which the host organism, transfected with the fragment, is grown. This is a copper promoter induction system. Alternatively, promoters induced by alcohol, glycolytic pathway, and carbon source can be selected.

It is preferred if the promoter is isolated as opposed to synthetic. Any of a variety of promoters can be selected, with it preferred that the promoter selected be derived from the organism that is to be transformed. For example, if a yeast cell is to be transformed to express the polypeptide, then it is preferred if the promoter is yeast derived. Promoter sequences which can be used in the present invention, include, but are not limited to: AOX1 (alcohol oxidase), which is inducible by methanol and is repressed when glucose or galactose is used as a carbon source; GAP (glyceraldehyde-3-phosphate dehydrogenase) providing a strong constitutive expression when the yeast is grown on glucose; FLD1 (glutathione-dependent formaldehyde dehygrogenase), a key enzyme when methylated amines are the nitrogen source and methanol, the carbon source for methyloptrophic yeasts; PEX 8 gene (peroxisomal matrix protein); and the YPT1 gene (encodes GTPase involved in secretion). The GAP promoter is one of the most commonly used in S. cerevisiae as well, but is of little use if the protein produced is toxic to the yeast. A list of suitable promoters is as follows:

Examples of promoters designed to obtain heterologous protein expression in yeasts. Yeast species indicated. Sc=*Saccharomyces cerevisiae*; Yl=*Yarrowia lipolytica*, So=*Schwanniomyces occidentalis*, Ps=*Pichis stipitis*, Pp=*Pichia pastoris*, Hp=*Hansenula polymorpha*, Kl=*Kluyveromyces lactis*

| Promoter | Yeast* | Reference |
|---|---|---|
| CYC1 | Sc | Cantwell et al., 1986[4] |
| ADH1 | Sc | Cantwell et al., 1986[4] |
| GAL7 | Sc | Buckholz & Gleeson, 1991[5] |
| ADH2 | Sc | Schuster, 1989[6] |
| GAPDH | Sc | Schuster, 1989[6] |
| LEU2 | Yl | Davidow et al., 1990[8] |
| XPR2 | Yl | Davidow et al., 1990[8] |
| TEF | Yl | Mueller et al., 1998[9] |
| RPS7 | Yl | Mueller et al., 1998[9] |
| URA3 | Yl | Davidow & DeZeeuw, 1991[7] |
| CUP1 | Sc | Hinnen et al., 1994[10] |
| ENO | Sc | Innis et al., 1985[11] |
| GAL1/GAL10 | Sc | Schulte et al., 1987[12] |
| GAPDH | Sc | Hallewell et al., 1987[13] |
| PGK | Sc | Kingsman et al., 1987[14] |
| PRO5 | Sc | Hori et al., 1990[15] |
| Mfoo1 | Sc | Brake et al., 1984[16] |
| GAM1 | So/Ps | Piontek et al., 1998[17] |
| XYL1 | So/Ps | Piontek et al., 1998[17] |
| ADH1 | So/Ps | Piontek et al., 1998[17] |
| PDC1 | So/Ps | Piontek et al., 1998[17] |
| AOX1$_p$ | Pp | Ogawa et al., 1999[18] |
|  | Hp | Raschke et al., 1996[19] |
| MOX$_p$ | Hp | Raschke et al., 1996[19] |
| FMD | Hp | Gellissen & Hollenberg, 1997[20] |
| GAP | Pp | Waterham et al., 1997[21] |
| FLD1 | Pp | Shen et al., 1998[22] |
| PEX8 | Pp | Johnson et al., 1999[23] |
| YPT1 | Pp | Sears et al., 1998[24] |
| LAC4 | Kl | Van den Berg et al., 1990[25] |
| PGK | Kl | Rocha et al., 1996[26] |
|  | Sc | Rocha et al., 1996[26] |
| CUP1 | Kl | Gellissen & Hollenberg, 1997[20] |
| Mfoo1 | Kl/Sc/Hp | Gellissen & Hollenberg, 1997[20] |
| CTTI | Kl | Gellissen & Hollenberg, 1997[20] |
| ADH4 | Kl | Saliola et al., 1999[27] |
| AMY1 | So | Piontek et al., 1998[17] |

It is also necessary to attach a transcription stop sequence to the fragment. This is done so as to stop transcription of the DNA fragment. Preferably, the transcription stop sequence is also derived from the host organism. Attachment typically occurs when the promoter is attached.

Any of a variety of methods can be used to attach a promoter to form the synthetic nucleic acid polymer. The preferred way to attach a promoter and a stop sequence to the synthetic peptide fragment is to clone the fragment for expressing the peptide into a plasmid containing the desired promoter and stop sequence. This is done by selecting a plasmid having available restriction nuclease sites the same as the synthetic fragment with the plasmid then cut with endonucleases and the fragment then cloned into the plasmid at the cut site. For example, as stated above, the preferred synthetic fragment has an Eco R1 site and a Not I site. Thus, a plasmid having a suitable promoter and stop sequence, and Eco R1 and Not I sites can be selected with the plasmid cut by the restriction endonucleases and the fragment cloned therein. It is preferred if the fragment is located proximal to the promoter in the plasmid. Any cut site can be used, with the sites designated, based on the plasmid of choice. There are well over 400 nucleases that can be used. It is also preferred if the plasmid includes an identifier. Such identifiers include:

MBP—maltose binding protein
His(6)—polyhistidine
MYC—transcription factor
GST—glutathione
S—transferase The promoter and synthetic peptide region that create the synthetic nucleic acid polymer will preferably contain a region that allows for testing of expression of the gene in a host organism. The identifier is desired because it allows for confirmation as to whether an organism has been transformed. An example of a suitable identifier is an myc epitope. This is a histidine site in the synthetic gene which means that the synthetic gene will express histidine. Thus, when a host is transformed, the transformation can be checked for by using a western blot that detects antibodies, such as polyhistidine. Other examples include markers inducing auxotrophy or antibiotic resistance.

Combining the promoter with the fragment and marker includes three different approaches:
(a) a zeocin selectable integrant;
(b) a URA 3 selectable integrant, which uses an auxotrophic marker such as HIS, Trp, LEU 1, or LEU 2; and,
(c) URA 3 selectable plasmid.

The preferred nucleic acid polymer has a GAPDH promoter, URA3 marker, a yeast stop sequence, and a nucleic acid polymer coding for a desired peptide or polypeptide. The expressed polypeptide is comprised of 3 methionine, 6 histidine, 6 lysine, 2 threonine, 2 isoleucine, 1 valine, and 1 tryptophan residues.

While a plasmid containing a stop sequence, promoter, and identifier is preferred, other methods can be used to attach the promoter to the nucleic acid molecule or polymer. An alternative method would include attaching a primer to the nucleic acid molecule, with the primer comprised of the promoter necessary to transcribe the nucleic acid molecule. Other methods may also be used as long as the promoter is attached to the fragment.

Once it has been determined that the synthetic nucleic acid polymer can be formed by cloning the fragment into a plasmid, it is necessary to amplify the synthetic polymer so as to have enough product to transform the desired host organism. The synthetic polymer or gene, comprised of the promoter, the nucleic acid polymer for expressing the peptide, the marker, and the stop sequence, is cut out of the plasmid. This is accomplished by again using a method involving different available restriction endonucleases. The gene fragment is then amplified using PCR. This is the preferred way to amplify the synthetic gene.

Once the synthetic gene is formed and in a sufficient amount, it is necessary to insert the gene into a host organism for expression. Any of a variety of means can be used to transform the host. It is most preferred to use a shuttle vector to transport the gene or nucleic acid polymer to the host and transform such host. Any of a variety of vectors are available for use in transferring the construct, including plasmids, cosmids, phagemids, and artificial chromosomes.

The synthetic gene can be cloned into a vector which can be used to transform the desired host organism. It is most preferred to use a plasmid yeast shuttle vector to transform the host yeast cells. Any of a number of plasmids can be used as long as the gene is transferred to the host, such host is transformed, and the gene can be expressed. In the present case, it has been observed that the synthetic gene can be blunt-end cloned into a yeast shuttle vector, such as a pRS 316 or 308 having Eco RV and Not I sites. These plasmids are preferred because they can confer an auxotrophic mutation. The plasmid vector is cut with a nuclease, and the synthetic gene is then blunt-end cloned into the vector to form a transformed vector. More specifically, it is preferred to double cut the plasmid with two nucleases to form a cut plasmid. Once the plasmid is cut by the enzymes, which typically occurs at 37° C. for two hours, the plasmid and gene are then ligated in the presence of the T4 ligase enzyme by melting the constituents for a period of time at a desired temperature, such as five minutes at 42° C. and then cooling to 16° C. for at least one hour. The plasmid product is purified and quantified, with a genetic vector construct formed.

In the case of yeast, a variety of 1.6–2.0 μm plasmid vectors are also available, which are epigenetic. Other suitable vectors insert the nucleic acid polymer into the nucleus or chromosome or ribosomal chromosomes. It is also preferred if the vector is a hybrid of a bacterial and yeast plasmid. Included in such a hybrid should be a sequence for bacterial and yeast replication. Preferably, the plasmid will contain ARS element vectors, which are designed to replicate independent of the genome and can increase to multiple copies often exceeding 20 per cell. Early ARS vectors were unstable and could be stabilized by addition of a yeast centromeric sequence (Romanos et al., 1992)[28]. More recently designed ARS vectors, such as those of the pINA type (Fournier et al., 1993)[29] and the pGC type (Muieller et al., 1998)[9] are relatively stable and are being used as high-copy number of expression vectors. Suitable plasmid vectors include, but are not limited to, pHIL-D2, pA0815, pPIC3K, pPICZ, pHW101, pGAPZ, pHIL-S1, pGApZ∞, pPIC9K, pPICZ∞, pIXY654, PDK1, pRBGO, pA0816, pA0817, pHWO18, PSS050, pSS040, pAR0815∞, pAR0815PDI, pHIL-D2pro1(III), pMP8, pMIVIST, pMIVINS, YEpB2plys.DELTA49, YEpZ100, YepZ100, YepZ415, pG12062, pGG5, pGG53, pGP3Hr, pGC69-3, pGC69-4, pXC69-4, pXX33, pXX22, pSP24, pLS-3, pC5aX3, pLD56, pLX-34, pPIC3X, pTL2M, pAS7/pAU5, and pSL2P3M.

After the vector construct is formed, it is necessary to transform the host organism with the vector. Any host that is suitable for use in an animal can be transformed. The host organism can be any of a variety of non-toxic eukaryotes, including fungi, or prokaryotes. More particularly, the host can be anything that can be consumed by the animal being fed. Most preferably, the host organism will be a yeast cell with available host yeast cells selected from the following genera: *Saccharomyces cerevisiae*, Pichia spp (including *P. pastoris* and *P. stipidis*) Yarrowia spp (including *Yarrowia lipolytica*,), Candida spp, Kluyveromyces ssp (including *K. waltii*, *K. lactis* and *K. drosophiliarium*), Zygosaccharomyces spp, *Schwannomyces occidentalis, Schizosaccharmyces pombe*, Hansenula spp (including *H. polymorpha*) and *Torulaspora delbrueckii*. The plasmids or vectors and host cells are incubated at a sufficient temperature and time to cause the vector to transfect the host cell.

Before producing the finished host product, it is preferred to test the host for expression of the gene. This is similar to testing the host to ensure transfection has occurred. An example of a useful testing method includes transforming a non-auxotrophic yeast strain. The construct, as mentioned, is auxotrophic (-URA), so that the transformation is theoretically easy to accomplish and an auxotrophic mutant is formed. The auxotrophic mutants are typically used as a testing system because this is considered comparatively easy. This results in an easy identification system which, in turn, permits easy determination of whether the host was transformed. Another example is to test for antibiotic resistance, which will be imparted to the host by the construct. In addition to the auxotrophic markers, a western blot or other techniques can be used to test for expression. For example, histidine should be expressed if the yeast cells have been transformed with a synthetic gene that codes for histidine. The western blot will use antibodies (polyhistidine $(His)_6$) to detect the presence of histidine. If transformation has occurred, as demonstrated by expression, it is then necessary to create an integration construct for insertion of the synthetic gene into yeast strains or other host organisms which will be used to express the desired peptide.

As mentioned, the integration construct is formed by isolating a linear construct from the cloned vector, whereby the construct will be comprised of the promoter, nucleic acid polymer for expression of the peptide, and part of the vector plasmid. Preferably, the auxotrophic (URA) marker or other marker gene will be included in the construct. In order to transfect the host, the following discussed steps are preferred. The construct is isolated by cutting the plasmid with the necessary nuclease and then amplifying with PCR. Next, the construct is prepared for insertion into the host. A gene site is identified in the host where the synthetic gene can be inserted. Primers are attached to the ends of the integration construct. The primers will form a homology region which will allow for the exchange of a chromosomal gene in the host for the synthetic gene. The homology region will be comprised of a number of non-transcribed base pairs. Generally, 40 base pairs should be homologous between the host chromosome and the integration construct, plus or minus 10 base pairs. Also, the primers that form the homology region will be 5' to 3' and 3' to 5'. The primers will be homologous to part of the synthetic gene and part of the gene in the host that will be exchanged with the synthetic gene. This will allow for a degree of homology between the construct and the host gene so as to allow for transformation. Once the primers are mixed with the synthetic gene, PCR is conducted to amplify the integration construct.

The integration construct is then ready to transform the host. The integration construct is placed in the transformation vector previously tested. Instead of a vector electroporation can be used to directly transform the host with the integration construct. The homologous region synthetic gene integration construct is then used to transform the yeast or host cells, with the yeast cells then selected for the transformance. The plasmid and host cells are simply incubated together. Following transformation of the yeast cells, it is necessary to mate the haploid host organisms, yeast strains, to produce a diploid yeast strain containing the synthetic gene.

Preferably, the organisms that are transformed are haploid, so that the yeast or host strains are mated to form a diploid strain. Haploid strains are used initially because this is comparatively an easier way to achieve transformation in the final host organism. Use of the haploid strain approach is advantageous because a homozygous strain is produced once the two haploid strains are mated. In particular, the gene is inserted into both strands. If a diploid cell is directly transfected, there is a risk that chromosomal segregation will occur, resulting in a number of generations that are homozygous and do not contain the desired integrant. Conversely, if an epigenetic plasmid approach is taken, then it is preferred to transfect a diploid cell. Once the transformation process is complete, stable transformed host organisms are selected for. An alternative to using an integration construct is to use 1.6 to 2 μm plasmids that have been isolated from Saccharomyces, Kluyvermoces, Torulaspora, or Zygosaccharomyces spp. Advantageously, these epigenetic plasmids are easy to get into the host. Ideally, the vector will result in multiple insertions into multi copy ribosomal DNA where many stable protein copies can be produced.

As such, transformation of the host cell generally follows, standard protocols (as discussed in Higgins and Cregg, 1997)[30], whereby the yeast, for example, and construct are mixed and then grown on a plate.

It is preferred for the synthetic gene to be inserted into the chromosome or maintained as an episomal plasmid. It is most preferred for the synthetic gene to be inserted into the chromosome.

Once the transformed organism is formed, it is necessary to grow the transformed organism for several generations to ensure that a sufficient population exists to produce the desired amount of polypeptides. Dependent upon whether the gene is inducible or constitutive, once a sufficient population is achieved, it may be necessary to induce the gene to produce the desired polypeptide.

The transformed organisms will express the peptide or protein. The expression product is either retained within the cytoplasm, attached to the cell wall, attached to the cell membrane, attached to any cellular organelle, or excreted into the medium in which the transformed organism is grown. If the protein is retained in or on the yeast or other host microorganism, then the entire host organism can be added to the feed as a supplement. If the protein is secreted, then the medium in which the host organisms were grown is added directly to the feed as a spray or other liquid, or as a dry application. It is most preferred if the host retains the expressed peptide or protein.

When the intact yeast or other microorganisms are added as a supplement, they can be added in microencapsulated form, added directly as a suspension of living organisms, or added after collection as a wet or dry cake of microorganisms for supplement. Microencapsulation includes encapsulation in materials that provide better access to the nutrient-providing organism, or that allow for the selection of a site for digestion, such as rumen by-pass materials. It should further be pointed out that production of the polypeptide will occur in such a manner that it will either be released into the broth in which the transformed organism is grown, released into the cytoplasm of the organism, or attached to the cell wall. As such, once sufficient peptide formation has occurred, the yeast or transformed organism can be added directly to the grain, or the host organisms can be separated from the broth, and the broth can then be added to the cereal grain. Alternatively, the peptides may be separated from the host organism and the broth in which it was grown, with the peptides then added directly to the cereal grain.

The transfected host does not have to be immediately expressed. Instead, the transfected host can be stored in a lyophilized form for a long period of time until needed.

The preferred transformed organism is non-toxic, suitable for consumption by animals, and expresses sufficient amounts of peptide or polypeptide to positively impact growth and health of animals fed the supplement. Preferably, the transformed organism is a yeast cell that is auxotrophic, has a synthetic gene located in its nucleus, and is haploid. The method and resultant products are illustrated in FIGS. 1–7.

EXAMPLES

Example 1

It was desired to form a synthetic gene that could be expressed to form a peptide comprised of amino acids desired for animal nutrition. As such, the process was initiated by selecting five enzymes produced by, including:

Kpn I-GGTAC/C, (SEQ ID NO: 1)

Bam H I-G/GATCC, (SEQ ID NO: 2)

Sal I-GTCGAC, (SEQ ID NO: 3)

Hind III-A/AGCTT, (SEQ ID NO: 4)

Not I-GC/GGCCGC. (SEQ ID NO: 5)

Additionally, four primers were ordered via the internet from Gibco/BRL/Life Technologies, Inc., with primers selected as follows:

Primer 1: is a 5' GAPDH Sal I

5' AAA AGT CGA CTC GAG TTT ATC ATT ATC AAT ACT CGC C 3' (SEQ ID NO: 6)

Primer 2: is a 3' GAPDH Nsi I—

5' GAT GAT GCA TCA TTT TGT TTA TTT ATG TGT GTT TAT TCG 3' (SEQ ID NO: 7)

Primer 3: is a 3' SYNPEP Not I—

5' AAA AGC GGC CGC CTA TTA CAT TTT AAT CTT AGT TTT CC 3' (SEQ ID NO: 8)

Primer 4: is a 5' SYNPEP Nsi I—

5' AAT GAT GCA TCA TCA TCA TCA CAA GAC AAA GAT C 3' (SEQ ID NO: 9)

The primers were suspended in sterile water to form a 100× stock having 50 nmoles/ microliter ($\mu$L). Thus, $$\frac{31.8 \text{ nmoles} \times 1000 \text{ }\mu\text{L}}{50 \text{ nmoles}} = 636 \text{ }\mu\text{L of H}_2\text{O}$$

As such, 636 $\mu$L of water was mixed with Primer 1, Primer 2 had 662 $\mu$L of H$_2$O added thereto, Primer 3 had 566 $\mu$L of H$_2$O added thereto, and Primer 4 had 708 $\mu$L of H$_2$O added thereto. After the primers were suspended in water, a cocktail for PCR to make a nucleic acid molecule that expresses the desired peptide was formed. The nucleic acid molecule was known as a synthetic peptide or Synpep. PCR is a standard reaction protocol used in the industry, which is known as a polymerase chain reaction.

In the cocktail, the following constituents were mixed:

| | |
|---|---|
| Water | 82.2 $\mu$L |
| Pfu Buffer (10x) | 10.0 $\mu$L |
| dNTPs (10 mm) | 2.0 $\mu$L |
| 5' Synpep Nsi I (50 ng/$\mu$L) | 5.0 $\mu$L |
| 3' Synpep Not I (50 ng/$\mu$L) | 5.0 $\mu$L |
| PFU Polymerase (2.5 $\mu$/$\mu$L) | 2.0 $\mu$L |

PCR Program No. 33 was selected. The Program cycles were as follows:

| | |
|---|---|
| 94° - 45 seconds | |
| 94° - 45 seconds | |
| 60° - 45 seconds | 30 cycles (all stages) |
| 72° - 30 seconds | |
| 72° - 10 minutes | |

By using the PCR, it was desired to form a nucleic acid molecule of approximately 69 base pairs (bp) and to produce an enhanced amount of product. After completion of the PCR, an analytical gel was run to check for the product band. A 1% gel was used with 1 kb and 30 bp markers. The analytical gel did not reveal the desired gene. As this was insufficient, the primers were checked to make sure the synthetic peptide and the primers did not overlap. It was determined that the product on the gel was a product of non-specific annealing.

Example 2

The same procedure as disclosed in Example 1 was followed except a 5' patch was ordered. The patch is a 50 bp patch and is the following nucleic acid sequence:

5' ATC ATC ACA AGA CAA AGA TCA AAA TGG TTT GGA AAA CTA AGA TTA AAA TG 3'. (SEQ ID NO: 10)

The PCR Program was run again with the cocktail having the following constituents:

| | |
|---|---|
| Water | 82.2 μL |
| Pfu Buffer (10x) | 10.0 μL |
| dNTPs (10 mm) | 2.0 μL |
| 5' Synpep Nsi I (50 ng/μL) | 5.0 μL |
| 3' Synpep Not I (50 ng/μL) | 5.0 μL |
| PFU Polymerase (2.5 μ/μL) | 2.0 μL |

PCR Program No. 33 was selected and slightly revised:

| | |
|---|---|
| 94° - 45 seconds | |
| 94° - 45 seconds | |
| 60° - 45 seconds | ] 30 cycles (all stages) |
| 72° - 30 seconds | |
| 72° - 10 minutes | |

The PCR product was then run on a 2% gel using the same markers as disclosed in Example 1. A product band of 68 bp was observed, and it was determined that the band was distinct and, therefore, there was no need for clean-up of the DNA.

The primer was suspended in 528 μL of $H_2O$.

Example 3

A GAPDH promoter (679 bp) was formed. A PCR cocktail was formed of the following constituents:

| | |
|---|---|
| Water | 76.0 μL |
| Pfu Buffer | 10.0 μL |
| dNTPs | 2.0 μL |
| Yeast DNA | 1.0 μL |
| 5' GAPDH Sal I (100x) | 5.0 μL |
| 3' GAPDH Nsi I (100x) | 5.0 μL |
| Pfu Turbo | 1.0 μL |
| | 100.0 μL |

PCR Program No. 34 was run:

| | |
|---|---|
| 94° - 1 minute | |
| 94° - 1 minute | |
| 61° - 1 minute | ] 30 cycles (all stages) |
| 72° - 1 minute | |
| 72° - 10 minutes | |

The PCR program was obtained from the suggested cycling parameters for PCR using PFU Turbo. After the PCR Program was finished, the product was checked on a 2% gel to see if the 679 bp band was formed. It was determined that no product was evident, and it was concluded that the PCR parameters needed to be changed, as well as using a different template.

Example 4

The same procedure as the previous Example 3 was followed, with the PCR cocktail as follows:

| | |
|---|---|
| Water | 75.0 μL |
| Pfu Buffer | 10.0 μL |
| dNTPs | 2.0 μL |
| Yeast DNA | 10.0 μL |
| 5' GAPDH Sal I (100x) | 1.0 μL |
| 3' GAPDH Nsi I (100x) | 1.0 μL |
| Pfu Turbo | 1.0 μL |
| | 100.0 μL |

PCR Program No. 34 was used, with it slightly revised compared to the program listed in Example 3. The Program was as follows:

| | |
|---|---|
| 95° - 5 minutes | |
| 94° - 1 minute | |
| 52° - 1 minute | ] 10 cycles (95°, 94°, 52°, and 72° stages) |
| 72° - 1 minute | |
| 94° - 1 minute | |
| 61° - 1 minute | ] 20 cycles (94°, 61°, 72°, and 72° stages) |
| 72° - 1 minute | |
| 72° - 10 minute | |

No product was located. It was determined that it may be necessary to change the template.

Example 5

The 68 bp product of Example 2 was then mixed in a PCR cocktail so as to, hopefully, produce an 85 bp product synthetic nucleic acid molecule for expressing desired peptides. The cocktail constituents were as follows:

| | |
|---|---|
| Water | 80.0 μL |
| Pfu Buffer (10x) | 10 μL |
| dNTPs (10 mm) | 2.0 μL |
| 5' Synpep Nsi I (50 ng/μL) | 1.0 μL |
| 3' Synpep Not I (50 ng/μL) | 1.0 μL |
| 68 bp Product (From Example 2) | 5.0 μL |
| Pfu Turbo | 1.0 μL |
| | 100.0 μL |

PCR Program No. 33 was conducted.

| | |
|---|---|
| 94°-1 minute | |
| 94°-1 minute | 10 cycles (94°, 94°, 49°, and 72° stages) |
| 49°-1 minute | |
| 72°-5 seconds | |
| 94°-1 minute | 20 cycles (94°, 60°, 72° and 72° stages) |
| 60°-1 minute | |
| 72°-5 seconds | |
| 72°-10 minutes | |

After completion of the PCR step, the product was run on a 2% gel to determine whether the Synpep of 85 bp was formed. It was determined that the synthetic nucleic acid molecule (Synpep 85 bp) was made.

Example 6

Next, a series of tests were performed to try and form a promoter:

1. PCR w/TAG

| template    | colony    | template    | 5 μL Yeast DNA |
|---|---|---|---|
| Water       | 15.0 μL   | Water       | 10.0 μL |
| Mg - buffer | 2.5 μL    | Mg - buffer | 2.5 μL |
| Mg Cl$_2$   | 3.5 μL    | Mg Cl$_2$   | 3.5 μL |
| 10$^x$ primers | 2.5 μL | 10$^x$ primers | 2.5 μL |
| Tag         | 0.5 μL    | Tag         | 0.5 μL |
| dNTPs       | 1.0 μL    | dNTPs       | 1.0 μL |

2. PCR w/Pfu Turbo

| template    | colony    | template    | 5 μL Yeast DNA |
|---|---|---|---|
| Water       | 25.0 μL   | Water       | 20.0 μL |
| Pfu buffer  | 2.5 μL    | Pfu buffer  | 2.5 μL |
| dNTPs       | 0.5 μL    | dNTPs       | 0.5 μL |
| 10$^x$ primers | 2.5 μL | 10$^x$ primers | 2.5 μL |
| Pfu Turbo   | 0.5 μL    | Pfu Turbo   | 0.5 μL |

PCR Program No. 34 GAPDH (same as before)

| | |
|---|---|
| 95°-5 minute | |
| 94°-1 minute | 10 cycles (95°, 94°, 52°, and 72° stages) |
| 52°-1 minute | |
| 72°-1 minute | |
| 94°-1 minute | 20 cycles (94°, 61°, 72°, and 72° stages) |
| 61°-1 minute | |
| 72°-1 minute | |
| 72°-10 minutes | |

Before products produced in the PCR reactions were run on a 2% agarose gel. It was found that the GAPDH promoter was formed. The promoter was a product equal to about 700 bp. The pGAPDH was cloned by PCR from S.C. genemic DNA using GAPDH promoter specific oligos.

Example 7

To cause ligation between the promoter and the synthetic nucleic acid molecule, it was necessary to extend the Synpep and promoter to cause overlap from 14 bp to 60 bp.

This was done to increase the rate of annealing. The primers for extension were a 3' link and a 5' link.

Cocktail:

| | |
|---|---|
| Water         | 155.0 μL |
| Mg - Buffer   | 20.0 μL |
| Mg Cl$_2$     | 16.0 μL |
| dNTPs         | 4.0 μL |
| 3' Link       | 2.0 μL |
| 5' GAPDH Sal I | 1.0 μL |
| Tag           | 1.0 μL |

PCR Program: Robocycler

| | |
|---|---|
| 94°-10 minutes | |
| 94°-45 seconds | 10 cycles (94°, 94°, 49°, and 72° stages) |
| 54°-30 seconds | |
| 72°-1 minute | |
| 94°-45 seconds | 20 cycles (94°, 60°, 72° and 72° stages) |
| 62°-30 seconds | |
| 72°-30 seconds | |
| 72°-10 minutes | |

The extended promoter (720 bp) was formed.

Example 8

Cocktail: 200 μL rxn

| | |
|---|---|
| Water          | 50.0 μL |
| Pfu buffer     | 20.0 μL |
| dNTPs          | 4.0 μL |
| Synpep (85 bp) | 20.0 μL |
| 5' Link        | 2.0 μL |
| 3' Synpep Not 1 | 2.0 μL |
| Pfu Turbo      | 2.0 μL |

Program No. 4: Extend

| | |
|---|---|
| 95°-5 minutes | |
| 94°-1 minute | 30 cycles (all stages) |
| 59°-30 seconds | |
| 72°-45 seconds | |
| 72°-10 minutes | |

A gel was run and the extended Synpep was formed.
Then PCR ligation of extended promoter and Synpep was conducted.
The PCR Cocktail was a 200 μL rxn, as follows:

| | | |
|---|---|---|
| Water | | 74.0 μL |
| Pfu buffer | | 20.0 μL |
| Template: | | |
| Promoter | (720 bp) | 50.0 μL |
| Synpep | (110 bp) | 50.0 μL |
| dNTPs | | 4.0 μL |
| Pfu Turbo | | 2.0 μL |
| 3' Synpep Not 1 | | 2.0 μL |
| Pfu Turbo | | 2.0 μL |

Program No. 5: Link

| | |
|---|---|
| 94°-1 minutes | |
| 94°-1 minute | 20 cycles (all stages) |
| 59°-1 minute | |
| 72°-45 seconds | |
| 72°-10 minutes | |

Next, a gel was run to see if a complete gene was formed. A 764 bp band was observed, which means the extended promoter was formed.

Example 9

The following ratios of amino acids would approximate the needed essential amino acids in corn based diets.

Obviously, as the diet ingredients change, the limiting amino acids would change. The amino acids are listed as a ratio, with the need for lysine set to equal 100. This would be congruent with the way amino acids are expressed on an ideal amino acid profile.

TABLE 1

|  | Poultry | Swine | Dairy Beef |
|---|---|---|---|
| Lysine | 100 | 100 | 100 |
| Methionine/Cysteine | 60 | 33 | 20 |
| Threonine | 60 | 0 | 0 |
| Valine | 75 | 0 | 0 |
| Isoleucine | 60 | 0 | 0 |
| Arginine | 80 | 0 | 100 |
| Tryptophan | 20 | 0 | 0 |
| Histidine | 0 | 0 | 35 |

TABLE 2

Ideal Indispensable Amino Acid Profiles (% of Lysine) of a Diet for Broiler Chicks in Two Age Categories[1]

|  | Days Posthatching | |
|---|---|---|
| Amino Acid | 0 to 21 | 21–49 |
| Lysine | 100 | 100 |
| Arginine | 105 | 105 |
| Histidine | 37 | 37 |
| Tryptophan | 16 | 17 |
| Isoleucine | 67 | 67 |
| Leucine | 111 | 111 |
| Valine | 77 | 77 |
| Phenylalanine + Tyrosine[2] | 105 | 105 |
| Methionine + Cysteine[3] | 72 | 75 |
| Threonine | 67 | 73 |
| Proline | 33 | 20 |
| Glycine (or Serine) | 67 | 50 |

[1]The listed ratios apply to digestible amino acid concentrations
[2]A minimum of 50% of the aromatic amino acids should be provided as phenylalanine
[3]A minimum of 50% of the sulfur-containing amino acids should be provided as methionine
This is referenced in Katz, R. S. and D. H. Baker. 1975. Journal of Animal Science 41:1355–1361

TABLE 3

Ideal Indispensable Amino Acid Profile (% Lysine) for Pigs in Three Separate Weight Categories

|  | Ideal Patterns (%) of Lysine | | |
|---|---|---|---|
| Amino Acid | 5 to 20 kg | 20 to 50 kg | 50 to 100 kg |
| Lysine | 100 | 100 | 200 |
| Threonine | 65 | 67 | 70 |
| Tryptophan | 18 | 19 | 20 |
| Methionine | 30 | 30 | 30 |
| Cystine | 30 | 35 | 40 |
| Methionine + Cystine | 60 | 62 | 65 |
| Isoleucine | 60 | 60 | 60 |
| Valine | 68 | 68 | 68 |
| Leucine | 100 | 100 | 100 |
| Phenylalanine + Tyrosine | 95 | 95 | 95 |
| Arginine | 42 | 36 | 30 |
| Histidine | 32 | 32 | 32 |

This is referenced in Baker, D. H. and T. K. Chung. 1990. Fermex Technical Review 6-4

TABLE 4

Metabolizable Amino Acid Requirements (grams/day) for Steers Gaining 2.3 kg per day at Two Body Weights

|  | Body Weight | |
|---|---|---|
| Amino Acid | 318 kg | 432 kg |
| Methionine | 17.0 | 17.4 |
| Lysine | 55.1 | 56.2 |
| Histidine | 21.3 | 21.8 |
| Phenylalanine | 30.6 | 31.3 |
| Tryptophan | 4.3 | 4.4 |
| Threonine | 34.1 | 34.9 |
| Leucine | 59.7 | 61.3 |
| Isoleucine | 25.4 | 26.1 |
| Valine | 35.7 | 36.6 |
| Arginine | 57.1 | 58.3 |

This is referenced in O'Connor et al. 1993. Journal of Animal Science

TABLE 5

Amino Acid Ratio (% of Lysine) Required to Supplement a Corn-Soybean Meal Diet for Swine (24% Soybean Meal)

| Amino Acid | % of Lysine |
|---|---|
| Lysine | 100 |
| Isolencine | 15 |
| Methionine + Cysteine | 100 |
| Phenylalanine + Tyrosine | 85 |
| Threonine | 56 |
| Tryptophane | 18 |
| Valine | 22 |

TABLE 6

Amino Acid Ration (% of Arginine) Required to Supplement a Corn-Soybean Meal Diet for Growing Ruminants (13% Crude Protein Diet).

| Amino Acid | % of Arginine |
|---|---|
| Arginine | 100 |
| Methionine | 9 |
| Lysine | 53 |
| Threonine | 9 |
| Histidine | 23 |

All of these peptide diet requirements can be produced by the present invention.

Example 10

The coding region of a synthetic peptide (SYNPEP) was constructed from synthetic DNA oligomers using a polymerase chain reaction (PCR). This was to be used to produce a yeast cell that expressed a peptide and was specifically designed for feeding poultry 0 to 21 days. The oligomers are listed below in Table 7.

TABLE 7

| PRIMER NAME | RESTRICTION SITE | SEQUENCE |
|---|---|---|
| 3' Synpep Not I | Not I | AAA AGC GGC CGC CTA TTA CAT TTT AAT CTT AGT TTT CC (SEQ ID NO: 8) |
| 5' Patch | none | ATC ATC ACA AGA CAA AGA TCA AAA TCG TTT GGA AAA CTA AGA TTA AAA TG (SEQ. ID NO: 10) |
| 5' Synpep EcoR I | EcoR I | AAT GGA ATT CAT GCA TCA TCA TCA TCA TCA CAA GAC AAA GAT C (SEQ ID NO: 11) |
| 5' pGAPZbHOint | none | TAT CCT CAT AAG CAG CAA TCA ATT CCA TCT ATA CTT TAA AAG ATC TTT TTT GTA GAA ATG (SEQ ID NO: 12) |
| 3' pGAPZbHOint | none | ACT TTT ATT ACA TAC AAC TTT TTA AAC TAA TAT ACA CAT TCC AGC TTG CAA ATT AAA GCC (SEQ ID NO: 13) |

Figure 2:
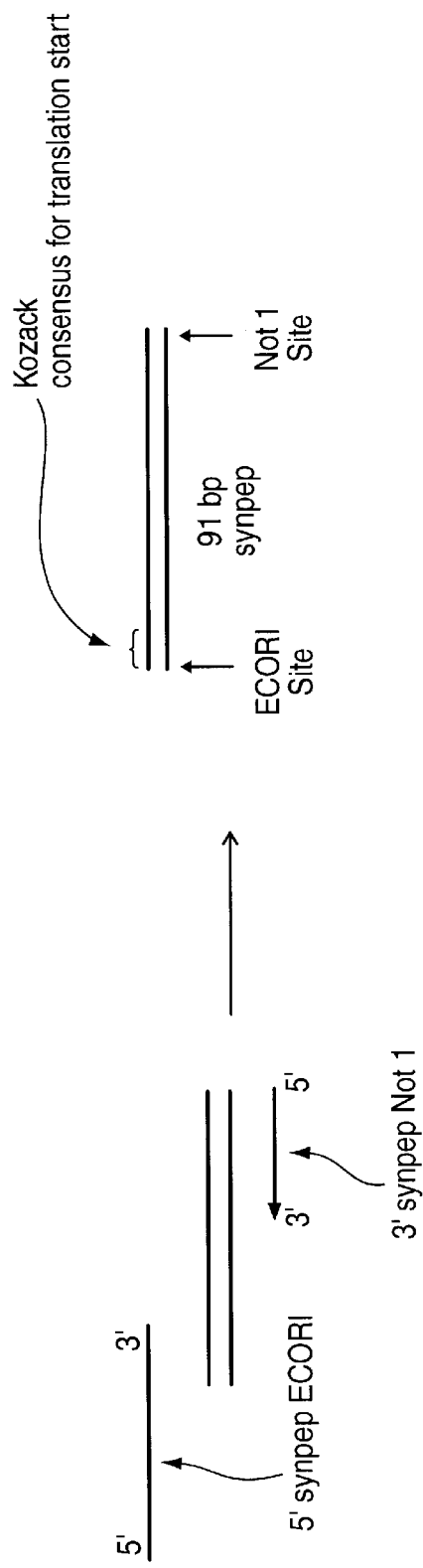
FIG. 2 shows the formation of a full length synthetic gene using the 68 bp primer dimer as a template.
Figure 3:
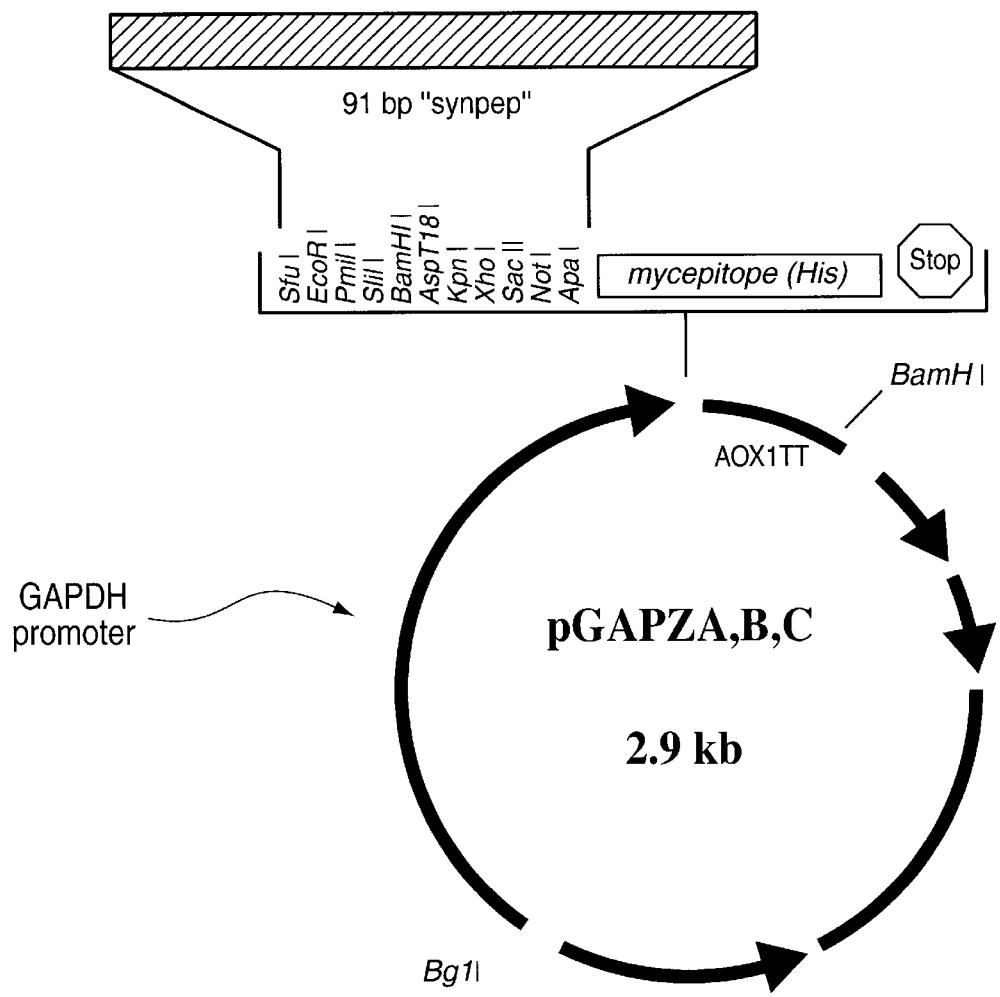
FIG. 3 shows the insertion of the synthetic peptide gene into a plasmid, having a stop sequence, a marker, and a promoter.
Figure 4:
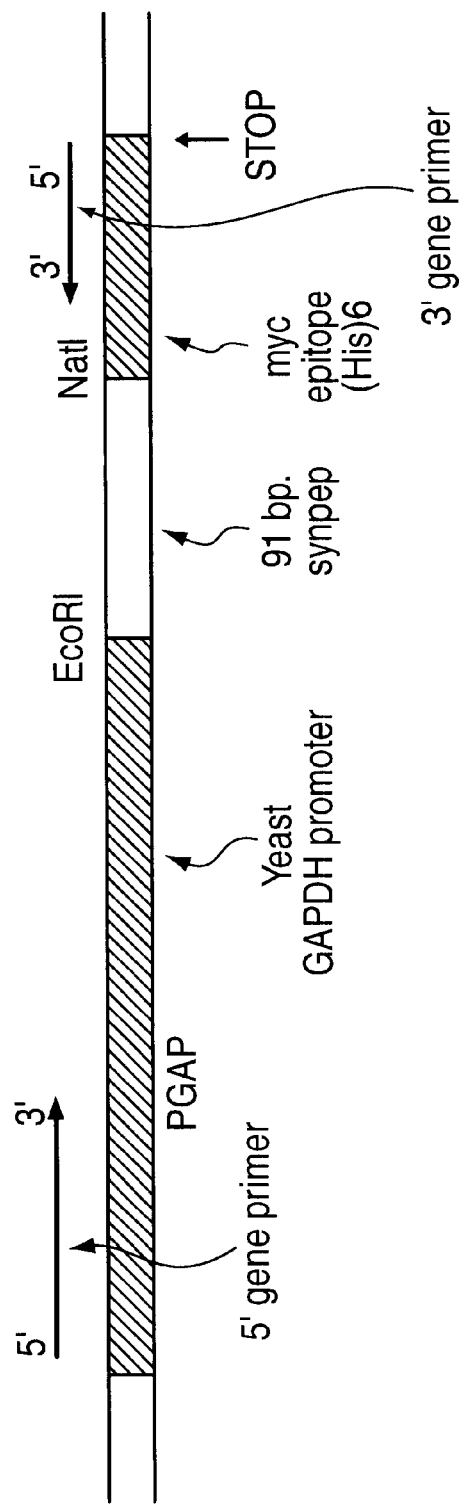
FIG. 4 illustrates a 698 bp synthetic gene product having a synthetic peptide and a promoter.
Figure 5:
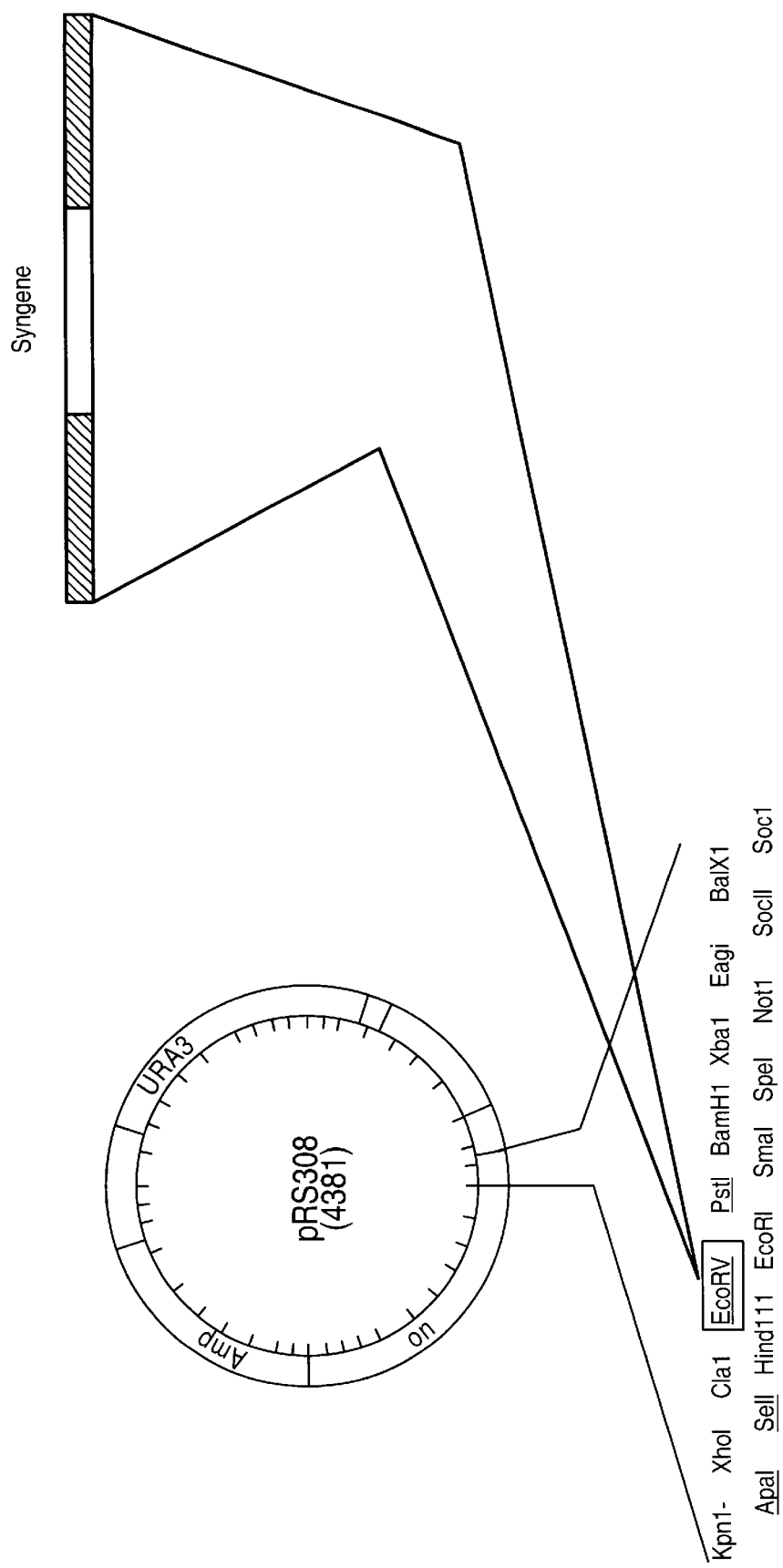
FIG. 5 shows the synthetic gene of FIG. 4 being blunt end cloned into a plasmid yeast shuttle vector pRS 308.
Figure 6:
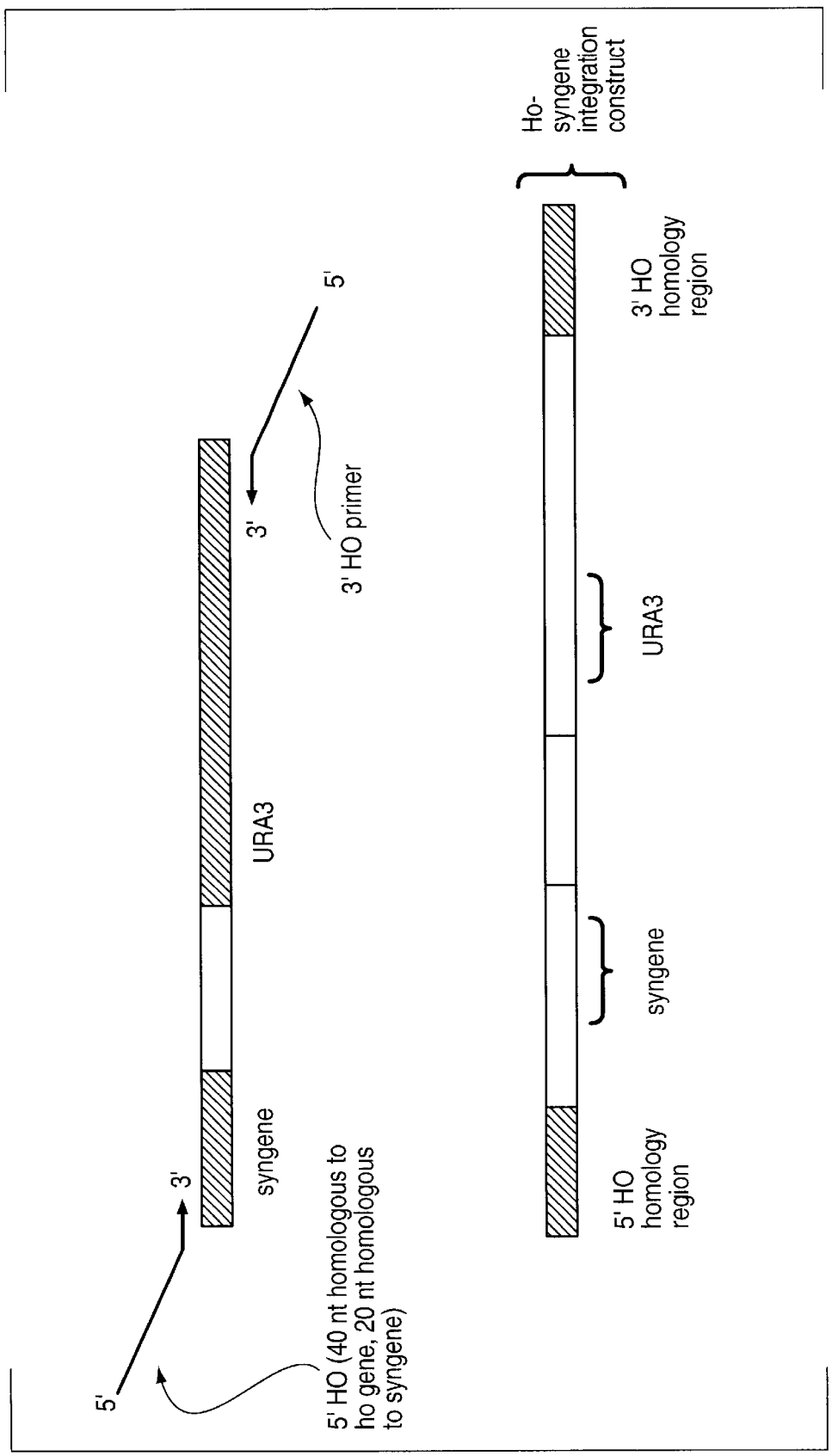
FIG. 6 shows an integration construct to be inserted into an HO gene side of a haploid yeast strain YJZ001a and YJZ001b.
Figure 7:
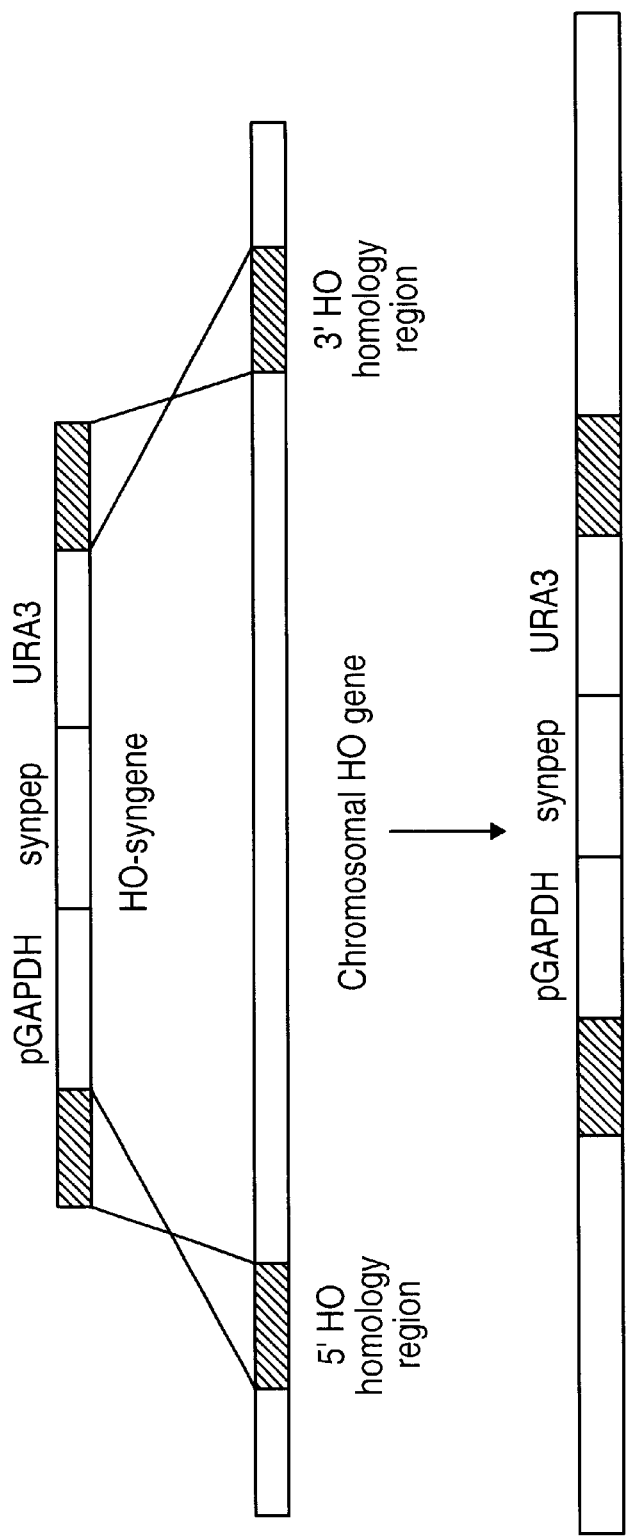
FIG. 7 shows the integration construct and portion of resultant transformed organism.
Figure 8:
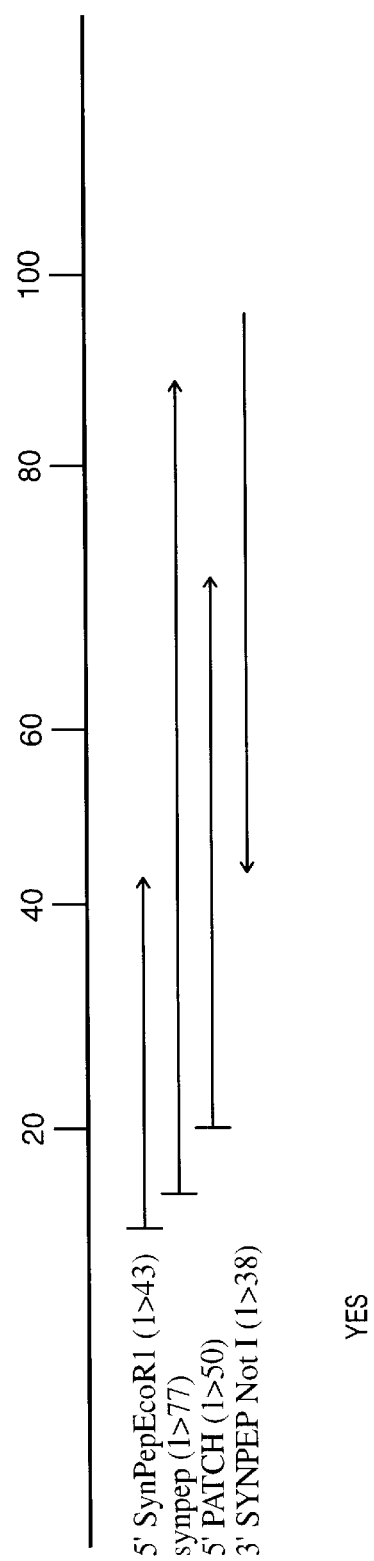
FIG. 8 shows an exemplary construct of various primers used to form the construct of the present invention; and, FIG. 9 shows an exemplary integration construct of the present invention.
Figure 9:
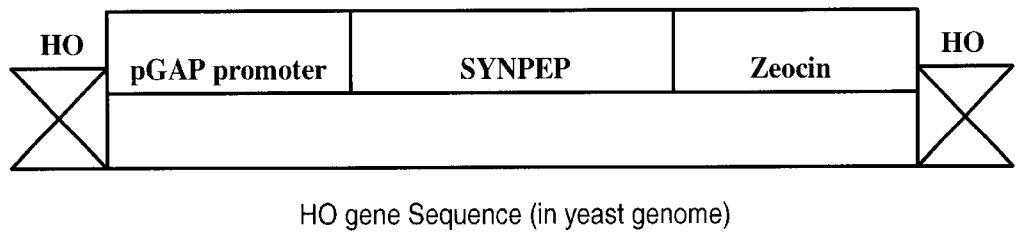

The construction of SYNPEP was a two-step procedure. In the first step, the 5' Patch and 3' SYNPEP Not I primers (Table 1) were used to generate a 68 bp DNA product. In the second PCR step, the 68 bp product was used as a template, along with the 5' SYNPEP EcoR I and 3' SYNPEP Not I (Table 1) primers, to produce the complete 85 bp SYNPEP coding region. The construct is illustrated in FIG. 1:

The SYNPEP open reading frame was ligated into the EcoRI and Not I sites of a vector pGAPZb (Invitrogen Corporation), which contained a heterologous glyceraldehyde-3-phosphate dehydrogenase (GAP) promoter from *Pichia pastoris*. The ligation mix was transformed into XL1-blue bacterial cells (Stratagene) and transformants were selected on Zeocin containing LB plates. Plasmid DNA were extracted from Zeocin resistant colonies and used as a template for the production of the pGAP-synpep integration construct. The linear integration fragment was amplified by PCR using the 5' pGAPZbHOint and 3' pGAPZbHOint primers (Table 1), which add 40 bp of HO gene specific DNA to the ends of the fragment to allow for homologous recombination. The integration construct is illustrated in FIG. 2.

*Saccharomyces cerevisiae* strain YPH501 (Mat a/α ura 3-52/ura3-52 lys2-801 amb/lys2-801 amb ade2-101 och/ade2-101 och trpl-Δ63 his3-Δ200/his3-Δ200 leu2-Δ1/leu2-Δ1) was transformed with the linear integration fragment and plated onto YPD (rich media) containing the antibiotic Zeocin. Those colonies that were Zeocin resistant were grown in YPD broth to an optical density of 0.8 to 1.2 at 600 nm. The cells were spun down, then resuspended into boiling Laemmli buffer (2% SDS, 10% glycerol, 50 mM DTT, 0.002% bromophenol blue, 62.5 mM Tris, pH 6.8) to extract intact proteins. Extracted proteins were applied to a nitrocellulose membrane using a dot blot manifold. Dot blots were probed with rabbit polyclonal IgG anti-His probe primary antibodies at 1:1000 dilution (Santa Cruz Biotechnology, #sc-803), followed by goat anti-Rabbit IgG HRP (horseradish peroxidase)—conjugated secondary antibodies at 1:1000 dilution (Pierce, #31460). The immunoblots were then developed using the Pierce SuperSignal West Pico Chemiluminescent Substrate and exposed to Kodak X-OMAT AR film for approximately 5 to 15 minutes. It was observed that expression of the Synpep peptide had occurred. Positive controls were polyhistidine peptides purchased from Santa Cruz Biotechnology (His-probe blocking peptide, #sc-803P). Known quantities of polyhistine peptide were applied to the same nitrocellulose blots to serve as internal standards for quantification.

As such, this Example shows at least one specific construction which can be used to form an animal feed.

Protein extracts were isolated from yeast cells containing the integrated gene fragment using hot Laemmli buffer. 100 μl of each sample were spotted onto a dot blot apparatus on a nitrocellulose membrane. Membranes were probed with rabbit anti-Polyhistidine IgG antibodies, then developed with a goat anti-rabbit IgG-HRP and a chemiluminescent substrate, as described in the text. The dot blot showed the expression of Synpep in yeast. The amount of peptide is estimated 27 μg/ml, based upon the intensity of the positive controls which contain known amounts of the polyhistidine. Another dot blot showing the expression of Synpep in several yeast strains.

REFERENCES

1 Birren, B., E. D., Green, S. Klapholz, R. M. Meyers, H. Tiethman, & F. Poskams. 1997a. Genome Analysis: A Laboratory Manual Vol. 1. Analyzing DNA. Cold Spring Harbor Press, Cold Spring Harbor, N.Y.
2 Birren, B., E. D., Green, S. Klapholz, R. M. Meyers, H. Tiethman, & F. Poskams. 1997b. Genome Analysis: A Laboratory Manual Vol. 2. Detecting Genes. Cold Spring Harbor Press, Cold Spring Harbor, N.Y.
3 Birren, B., E. D., Green, S. Klapholz, R. M. Meyers, H. Tiethman, & F. Poskams. 1997c. Genome Analysis: A Laboratory manual Vol. 3. Cloning Systems. Cold Spring Harbor Press, Cold Spring Harbor, N.Y.
4 Cantwell, B A., G. Brazil, N. Murphy, & D. J. McConnell. 1986. Comparison of expression of the endobeta-1,3-1, 4-glucanase gene from *Bacillus subtilis* in *Saccharomyces cerevisiae* from the CYC1 and ADH1 promoters. Curr. Genet. 11:65–70.
5 Buckholz, R. G. and M. A. G. Gleeson. 1991. Yeast systems for the commercial production of heterologous proteins. Bio/Technol. 9:1067–1072.
6 Schuster, J. R. 1989. Regulated transcriptional systems for the production of proteins in yeast: regulation by carbon source. Pp. 83–108 In Barr, P. J., Brake, A. J. & Valenzuela, P. (Eds). Yeast Genetic Engineering Butterworth Publishers, Stoneham, Mass.
7 Davidow, L. S. & J. R. DeZeeuw. 1991. Process for integrative transformation of *Yarrowia lipolytica*. U.S. Pat. No. 5,071,764
8 Davidow, L. X., J. r. Dezeeuw, & A. E. Franke. 1990. Expression and secretion of heterologous proteins by *Yarrowia lipolytica* transformants. U.S. Pat. No. 4,937,189.

9 Muiller, S., T. Sandal, P. Kamp-Hasen and H. Dalboge. 1998. Comparison of expression systems in yeasts *Saccharomyces cerevisiae, hansenula polymorpha, Kluyveromyces lactis, Schizosaccharomyces pombe* and *Yarrowia lipolyticacloning* of two novel promoters from *Yarrowia lipolytica.* Yeast 14:1267–1298.

10 Hinnen, A., F. Buxton, B. Chaudhyuri, J. Hiem, T. Hottiger, B. Meyhack, & G. Pohlig. 1994. Gene expression in recombinant yeast. Pp. 121–193 In: Smith, A. (Ed.O Gene expression in Recombinant Microorganisms. Marcel Dekker, New York, N.Y.

11 Innis, M. A., M. J. Holland, P. C. McCabe, G. E., Cole, V. P. Wittmann, R. Tal, K. W. K. Watt, K. D. H. Gelfand, J. P. Holland & J. H. Meade. 1985. Expression, glycosylation and secretion of an Aspergillus glucoamylase by *Saccharomyces cerevisiae.* Science 228:21–26.

12 Schulte, L. D., J. Tanner, K. J. Hofmann, E. A. Emini, J. H. Condra, R. E. Jones, E. Kieff, & R. W. Ellsi. 1987. Expression and secretion in yeast of a 400-kDa-envelope glycoprotein derived from Epstein-Barr virus. Gene 54:113–123.

13 Hallewell, R. A., R. Mills, P. Tekamp-Olson, R. Blacher, S. Rosenberg, F. Otting, F. R. Masiarz, & C. J. Scandella. 1987. Amino terminal acetylation of authentic human Cu, Zn superoxide dismutase produced in yeast. Biotechnology 5:363–366.

14 Kingsman, S. M., D. Cousens, C. A. Stanway, A. Chambers, M. Wilson, & A. J. Kingsman. 1990. High-efficiency yeast expression vectors based on the promoter of the phosphoglycerate kinase gene. Methods Enzymol. 185:329–341.

15 Horii, H., H. Kawabe, H. Arimuira, H. Mukai, K. Kobayashi, M. Tsujikawa, m. Nishida, & T. Suyama. 1990. Yeast promoter and process for preparing heterologous protein. U.S. Pat. No. 4,945,046

16 Brake, A. J., J. P. Merryweather, D. G. Coit, U. A. Heberlein, F. R. Masiarz, G. T. Mullenbach, M. S. Uredea, P. Valenzuela, & P. J. Barr. 1984. factor-directed synthesis and secretion of mature foreign proteins in *Saccharomyces cerevisiae.* Proc. Natl. Acad. Sci. USA 81:4642–4646.

17 Piontek, M., J. Hagedon, C. P. Hollenberg, G. Gellissen, & A. W. M. Strasser. 1998. Two novel gene expression systems based on the yeasts *Schwanniomyces occidentalis* and *Pichia stipitis.* Appl. Microbiol. Biotechnol. 50:331–338.

18 Ogawa, M., S. Nakamura, T. Atscuhi, T. Tamiya, T. Tsuchiya & S. Naki. 1999. Macromolecular antimicrobial glycoprotein, achacin, expressed in a methlotrophic yeast *Pichia pastoris.* FEBS Letters. 488:41–44.

19 Raschke, W. C., B. R. Neiditch, M. Hendricks, & J. Creeg. 1996. Inducible expression of a heterologous protein in *Hansenula polymorpha* using the alcohol oxidase 1 promoter of *Pichia pastoris.* Gene 177:163–167.

20 Gellisen, G., & C. P. Hollenberg. 1997. Application of yeasts in gene expression studies: a comparison of *Saccharomyces cerevisiae, Hansenula polymorha* and *Kluyveromyces lactis*-a review. Gene 190:87–97.

21 Waterham, H. R., M. E. Digan, P. J. Koutz, S. V. Lair, & J. M. Cregg. 1997. Isolation of the *Pichia pastoris* glyceraldehyde-3-phosphate dehydorgenase gene and regulation and use of its promoter. Gene 186:37–44

22 Shen, S., G. Sulter, T. W. JHEFFRIES<J. M. Cregg. 1998. A strong nitrogen source-regulated promoter for controlled expression of foreign genes in the yeast *Pichia pastoris.* Gene 216:93–102.

23 Johnson, M. A. H. R. Waterham, G. P. Ksheminska, L. R. Fayura, J. S. Cereghino, O. V. Stasyk, M. Veenhuis, A. R. Kulachkovsky, A. A. Sibimy, & J. M. Cregg. 1999 Genetics 151:1379–1391.

24 Sears, I. B., J. O'Connor, O. W. Rossanese, & B. S. Glick. 1998. A versatile set of vectors for constitutive and regulated gene expression in Pichiapastoris. Yeast 14:783–790.

25 Van den Berg, J. A., K. J. van der Laken, A. J. van Ooyen, T. C. H. M. Renniers, K. Reitveld, A. Schaap, A. J. Brake, R. J. Bishop, K. Schultz, D. Moyer, M. Richman, & J. r. Schuster. 1990. Kluyveromyces as a host for heterologous gene expression: Expression and secretion of prochymosin. Bio/Technology 8:135–139.

26 Rocha, T. L., G. Paterson, K. Crimmins, A. Boyd, L. Sawyer, & L. A. Fothergill-Gilmore. 1996. Expression and secretion of recombinant ovine β-lactoglobin in *Saccharomyces cerevisiae* and *Kluyveromyces lactis.* Biochem. J. 313:927–932.

27 Saliola, M., C. Mazzoni, N. Solimando, A. Crisa, C. Falcone, G. Jung, & R. Fleer 1999. Use of the KIADH4 promoter for ethanol-dependent production of recombinant human serum albumin in *Kluyveromyces lactis.* Appl. Environ. Microbiol. 65:53–60.

28 Romanos, M. A., C. A. Scorer, & J. J. Clare. 1992. Foreign gene expression in yeast: a review. Yeast 8:423–488.

29 Fournier, P., C. Gaillardin, B. Kudla, & H. Heslot. 1993. ARS sequence which is efficacious in *Yarrowia lipolytica.* U.S. Pat. No. 5,212,087.

30 Higgins, D. R. & J. M. Cregg. 1997. Pichia protocols: Methods in Molecular Biology Vol. 103. Humana Press Inc. Totowa, N.J.

31 Gait, M. J. and Sheppard, R. C. "Rapid synthesis of oligodeoxyribonucleotides: a new solid—phase method." Nucleic Acids Research, 4: 1135–1158 (1977).

Thus, there has been shown and described a method for producing a genetically modified yeast organism which fulfills all of the objects and advantages sought therefor. It will be apparent to those skilled in the art, however, that many changes, variations, modifications, and other uses and applications for the subject methods and compositions are possible, and also changes, variations, modifications, and other uses and applications which do not depart from the spirit and scope of the invention are deemed to be covered by the invention which is limited only by the claims which follow.

What is claimed is:

1. An animal feed for use in feeding an animal, comprising:
   (a) an amouint of grain containing a plurality of arnino acids in quantities requiring supplementation to achieve a desired quantity of amino acids for dietary requirements of the animal; and,
   (b) an amount of a transformed organism selected from the group consisting of non-toxic fungi and non-toxic bacteria wherein said transformed organism comprises a synthetic gene comprising a promoter operatively linked to a coding sequence designed to encode a peptide comprising amino acids necessary to achieve the desired quantity of amino acids for at least one type of amino acid.

2. The animal feed of claim 1 wherein said transformed organism is a transformed yeast strain.

3. The animal feed of claim 1 wherein said amount of said transformed organism contains sufficient amino acids to provide a complete supplement achieving the desired amino acid content with respect to all amino acids in the desired quantity of amino acids.

4. The animal feed of claim 1 wherein said transformed organism is a yeast strain, and said promoter comprises a yeast promoter.

5. The animal feed of claim 1 wherein said peptide is at least two amino acids long.

6. The animal feed of claim 1 wherein said peptide comprises at least two different amino acids necessary to achieve the desired quantity of amino acids.

7. The animal feed of claim 1 wherein said grain comprises a cereal grain selected from the group consisting of soybean, corn, barley, rice, wheat, oats, millet, maize, sunflower, canola, grass, and combinations thereof.

8. The animal feed of claim 1 wherein said peptide comprises at least five different amino acids necessary to achieve the desired quantity of ammo acids.

9. The animal feed of claim 1 wherein said at least one type of amino acid comprises lysine and said animal feed comprises 100% of lysine in said desired quantity of amino acids.

10. A method for mnaking an animal feed, the method comprising the steps of:
    selecting a grain that contains a plurality of amino acids in quantities requiring supplementation to achieve a desired quantity of amino acids for dietary requirements of the animal,
    producing a transformed organism selected from the group consisting of non-toxic fungi and nontoxix bacteria, the transformed organism having a synthetic gene comprising a promoter operatively linked to a coding sequence designed to encode a peptide comprising nmno acids necessary to achieve the desired quantity of amino acids for at least one type of amino acid; and mixing the grain with the transformed organism in amounts that achieve the desired quantity of amino acids, whereby an animal feed is made.

11. The method of claim 10 wherein said promoter is selected from the group consisting of: CYC1, ADH1, GAL7, ADH2, GAPDH, LEU2, XPR2, TEF, RPS7, URA3, CUP1, ENO, GAL1/GAL10, PGK, PHO5, MfooI, GAM1, XYL1, PDC1, $AOX1_p$, $MOX_p$, FMD, GAP, FLD1, PEX8, YPT1, LAC4, PGK, CTT1, ADH4, and AMY1.

12. The method of claim 10 wherein said promoter is selected from the group consisting of AOX1, GAP, FLD1, PEX8, YP71, and GAPDH.

13. The method of claim 10 wherein said host organism used in said step of producing said transformed organism comprises a yeast strain.

14. The method of claim 10 wherein said step of producing said transformed organism comprises creating gene construct comprising said synthetic gene and wherein said gene construct is selected from the group consisting of epigenetic constructs, inserts into ribosornal DNA, and inserts into host genome.

15. The method of claim 10 wherein said peptide is comprised of at least five different amino acids.

16. The method of claim 10 wherein said step of producing said transformed organism comprises using a yeast promoter as said promoter.

17. The method of claim 16 wherein said yeast strain is selected from the group consisting of *Saccharomyces cerevisiae, Pichia pastoris, Pichia stipidis*, Yarrowia species plural (spp), Candida spp, *Kluyveromyces waltii, Kluyveromyces lactis, Kluyveromyces drosophiliarium*, Zygosaccharomyces spp, *Schwannomyces occidentalis, Schizosaccharmyces pombe*, Hansenula spp, and *Torulaspora delbrueckii*.

18. The method of claim 10 wherein said step of producing said transformed organism comprises inserting said synthetic gene into a transfer vector.

19. The method of claim 18 wherein said transfer vector used in said step of inserting said synthetic gene is selected from the group consisting of plasmids, cosmids, phagemids, and artificial chromosomes.

20. The method of claim 19 wherein said promoter is selected from the group consisting of constitutive promoters and inducible promoters.

* * * * *